(12) United States Patent
Rega

(10) Patent No.: US 8,242,189 B2
(45) Date of Patent: Aug. 14, 2012

(54) SILICONE-URETHANE COPOLYMERS

(75) Inventor: Joseph Rega, Wilmington, MA (US)

(73) Assignee: AdvanSource Biomaterials Corporation, Wilmington, MA (US)

( * ) Notice: Subject to any disclaimer, the term of this patent is extended or adjusted under 35 U.S.C. 154(b) by 0 days.

(21) Appl. No.: 12/903,440

(22) Filed: Oct. 13, 2010

(65) Prior Publication Data

US 2011/0086940 A1     Apr. 14, 2011

Related U.S. Application Data

(60) Provisional application No. 61/251,028, filed on Oct. 13, 2009.

(51) Int. Cl.
    *C08K 3/10*         (2006.01)
    *C08K 3/40*         (2006.01)
    *C08F 283/02*     (2006.01)

(52) U.S. Cl. ........ 523/122; 523/113; 524/403; 524/413; 524/423; 524/442; 525/453

(58) Field of Classification Search .................. 523/113, 523/122; 524/403, 413, 423, 442; 525/453
See application file for complete search history.

(56) References Cited

U.S. PATENT DOCUMENTS

| | | | |
|---|---|---|---|
| 4,657,964 A | 4/1987 | Lai et al. | |
| 5,272,012 A | 12/1993 | Opolski | |
| 5,530,083 A | 6/1996 | Phelps et al. | |
| 5,756,214 A | 5/1998 | Waldron et al. | |
| 5,863,627 A * | 1/1999 | Szycher et al. | 428/36.8 |
| 6,313,254 B1 | 11/2001 | Meijs et al. | |
| 6,627,724 B2 | 9/2003 | Meijs et al. | |
| 7,026,423 B2 | 4/2006 | Gunatillake et al. | |
| 7,772,296 B2 | 8/2010 | Garey, Jr. et al. | |
| 2003/0092864 A1 * | 5/2003 | Gunatillake et al. | 528/26 |
| 2008/0033522 A1 * | 2/2008 | Grewe et al. | 623/1.11 |

OTHER PUBLICATIONS

CarboSil product description (2009), http://www.dsm.com/en_US/downloads/dbm/pdf006, 2 pages.

"Table I. Chronology of biomedical silicone-modified polyurethane development" and "Table II. Structure and properties of some members of three new families of thermoplastic silicone-urethane copolymers (TSPUs) compared with related biomedical polyurethanes" [online]. *Medical Device Link*, 2000 [retrieved on Oct. 9, 2009], 2 pages.

Ward, "Thermoplastic Silicone-Urethane Copolymers: A New Class of Biomedical Elastomers" [online]. *Medical Device Link*, 2000 [retrieved on Feb. 22, 2011], 9 pages.

* cited by examiner

*Primary Examiner* — Kriellion Sanders

(74) *Attorney, Agent, or Firm* — K&L Gates LLP

(57) ABSTRACT

The invention relates to silicone-urethane copolymers and methods for making the copolymers. The silicone-urethane copolymers can have many physical properties usually associated with polyurethanes but also the feel and characteristics of silicones.

20 Claims, No Drawings

SILICONE-URETHANE COPOLYMERS

CROSS REFERENCE TO RELATED APPLICATIONS

This application claims priority to and the benefit of U.S. Provisional Patent Application Ser. No. 61/251,028, filed on Oct. 13, 2009, the disclosure of which is incorporated by reference herein in its entirety.

FIELD

The present teachings generally relate to thermoplastic polymers and more particularly, to thermoplastic polyurethanes.

BACKGROUND

There is a need for polymers which offer the feel and characteristics of silicones but also exhibit physical properties expected of polyurethanes such as elasticity and melt-processability.

SUMMARY

The present teachings relate to silicone-urethane copolymers and methods for making the copolymers. More specifically, the present teachings relate to biocompatible and bio-durable silicone-urethane copolymers having a high silicone content and desirable properties that are characteristic of both silicones and polyurethanes. For example, the present copolymers can be elastomeric like conventional silicones, but at the same time are thermoplastic and can have good mechanical properties like conventional polyurethanes.

In various embodiments, the present silicone-urethane copolymers can be the reaction product of a one-step reaction of reactants comprising a diisocyanate, a polycarbonate diol, a polysiloxane, a $C_{2-8}$ diol chain extender, and optionally a monofunctional siloxane chain terminator. The resulting copolymers can include polycarbonate internal segments, polysiloxane internal segments, polyurethane internal segments, and siloxane terminating segments. In certain embodiments, the diisocyanate can be selected from an aliphatic diisocyanate, an alicyclic diisocyanate, and an alicyclic-aliphatic diisocyanate. For example, the diisocyanate can be an aliphatic diisocyanate such as hexamethylene-1,6-diisocyanate, or an alicyclic-aliphatic diisocyanate such as dicyclohexylmethane-4,4'-diisocyanate. In certain embodiments, the polysiloxane can be a dihydroxyalkyl-terminated polydialkylsiloxane such as a dihydroxypropyl-terminated polydimethylsiloxane. The polysiloxane can have a molecular weight between about 500 Da and about 8000 Da, and preferably between about 1000 Da and about 2500 Da. The present copolymers generally comprise a high siloxane content. Typically, the present copolymers can comprise at least about 5% by weight, at least about 10% by weight, at least about 15% by weight, at least about 18% by weight, at least about 20% by weight, at least about 25% by weight, and at least about 30% by weight of the polysiloxane. In particular embodiments, the copolymers can include an antimicrobial additive, specifically, a silver-containing additive. For example, the silver-containing additive can be in the form of silver ions associated with a zirconium phosphate carrier or a silver-containing silica glass powder. The copolymers also can include barium sulfate, micronized silica, or both.

In another aspect, the present teachings relate to a method of making a silicone-urethane copolymer. The method comprises admixing a reaction mixture comprising a diisocyanate, a polycarbonate diol, a polysiloxane, a $C_{2-8}$ diol chain extender, and optionally a monofunctional siloxane chain terminator under an inert gas in the presence of a catalyst to initiate a one-step polymerization reaction. The temperature of the reaction mixture is monitored, and the admixing step is terminated when the reaction mixture reaches a predefined temperature. In some embodiments, the method further comprises curing the silicone-urethane copolymer, for example, by heating in an oven for a suitable period of time to ensure completion of the reaction.

DETAILED DESCRIPTION

Throughout the application, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present teachings remain operable. Moreover, two or more steps or actions may be conducted simultaneously.

In brief overview, polyurethanes are polymers having organic subunits connected by a urethane (carbamate) linkage. A urethane linkage can be produced by reacting an isocyanate (R—N=C=O) with an alcohol (R'—OH). As used herein, R, R', R", and so forth represent an organic group unless specifically defined otherwise. In the simplest example, a diisocyanate and a diol will react to form a compound containing a urethane linkage, i.e., —NHC(O)O—. Thus, the reaction mechanism, in general, can be described as:

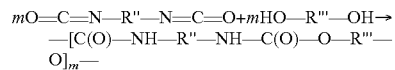

Polyurethanes can have what often are referred as "hard" and "soft" segments. Hard segments usually are reaction products of a diisocyanate and a chain extender (e.g., a low molecular weight diol or diamine) and the soft segments are polyalcohols (polyols) with terminal hydroxyl groups.

To prepare the present copolymers, a polyisocyanate is reacted with one or more chain extenders, and at least two types of polyols, e.g., a polycarbonate diol and a dihydroxy-terminated silicone (polysiloxane) in the presence of a catalyst. In certain embodiments, the relative ratios of the different components are adapted such that in addition to being internal segments, the polyols also function as the terminating groups. Optional additives can be included in the copolymers depending on the intended use of the copolymers. Each of the components will be described in more detail below.

The polyisocyanate for preparing the present copolymers can be any polyisocyanate having at least two isocyanate groups, but preferably a diisocyanate having two terminal isocyanate groups. In most embodiments, the polyisocyanate can be a diisocyanate represented by the formula $O=C=N-R^1-N=C=O$, wherein $R^1$ is an organic group selected from aliphatic, alicyclic, aliphatic-alicyclic, aromatic, and aliphatic-aromatic hydrocarbon groups containing from 4 to 26 carbon atoms, preferably from 6 to 20 carbon atoms, more preferably from 6 to 14 carbon atoms. Representative examples of such diisocyanates include tetramethylene-1,4-diisocyanate, hexamethylene-1,6-diisocyanate (HDI), dicyclohexylmethane-4,4'-diisocyanate (HMDI), trimethyl-hexamethylene-2,4,4-diisocyanate (and isomers), m-tetramethylxylene diisocyanate, dimer acid diisocyanate (e.g., lysine diisocyanate), isophorone diisocyanate, m-xylene diisocyanate, diethylbenzene diisocyanate, decamethylene-1,10-diisocyanate, cyclohexane-1,2-diisocyanate, cyclohexane-1,4-diisocyanate, toluene-2,4-diisocyanate; toluene-2,6-diisocyanate; m-phenylene diisocyanate; hexahydrotoluene-2,4-diisocyanate (and isomers), naphthalene-1,5-diisocyanate; 1-methoxyphenyl-2,4-diisocyanate, diphenylmethane-4,4'-diisocyanate, biphenylene-4,4'-diisocyanate, 3,3'-dimethoxy-4,4'-biphenylene diisocyanate, 3,3'-dimethyl-4,4'-biphenylene diisocyanate, and mixtures thereof. In preferred embodiments, the diisocyanate is an aliphatic diisocyanate such as hexamethylene diisocyanate (HDI), or an alicyclic-aliphatic diisocyanate such as dicyclohexylmethane-4,4'-diisocyanate (HMDI). In a particularly preferred embodiment, the diisocyanate is HMDI.

The polyalcohols or polyols for preparing the present copolymers can include a polycarbonate polyol, which typically can be more stable than traditional polyols such as polyether glycols when implanted in the human body. Polycarbonate polyols (or polycarbonate glycols) useful in making the present copolymers can have a molecular weight from about 500 Da to about 5000 Da, preferably from about 650 Da to about 3500 Da, more preferably from about 1000 Da to about 2500 Da, and can have the following formula:

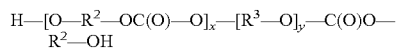

$H-[O-R^2-OC(O)-O]_x-[R^3-O]_y-C(O)O-R^2-OH$ wherein $R^2$ is a divalent aliphatic, aliphatic-alicyclic, or alicyclic group having 4 to 40 carbon atoms, $R^3$ is a linear aliphatic group having 2 to 8 carbon atoms optionally substituted with pendant groups, x is an integer from 2 to 20, and y is an integer from 0 to 20. The polycarbonate polyol can have few ether linkages. For example, x can be an integer from 10 to 20, and y can be an integer from 0 to 4. A preferred polycarbonate glycol is a dihydroxy-terminated linear aliphatic polycarbonate diol (i.e., both $R^2$ and $R^3$ are linear aliphatic groups). In certain embodiments, traditional polyols such as polypropylene glycols, polyethylene glycols, polybutylene glycols (or polytetramethylene oxide PTMO); dihydroxy-terminated polyester, and diamine-terminated polyalkylene glycols also can be used.

Suitable chain extenders include low molecular weight diols and diamines. In certain embodiments, only one type of chain extenders is used. In certain embodiments, two or more different types of chain extenders (e.g., two different diols, two different diamines, one diol and one diamine, and so forth) can be used. In particular embodiments, the chain extender can be a low molecular weight diol, although triol or high-order alcohols such as glycine also are contemplated to be within the scope of the present teachings. The diol chain extender which is useful in the present copolymer can have from 2 to 8 carbon atoms (e.g., a $C_{2-8}$ diol) which are preferably in a straight chain but in some embodiments, can have optional side groups such as methyl or ethyl. Exemplary of suitable diol chain extenders include ethylene glycol, diethylene glycol, triethylene glycol, 1,4-butane diol, neopentyl glycol, 1,6-hexanediol, 1,8-octane diol, 1,2 and 1,3-propylene glycol, 2,3-butylene glycol, dipropylene glycol, dibutylene glycol, and mixtures thereof. Preferably, the low-molecular weight diol used as the chain extender is 1,4-butane diol. Additionally, polyamines such as diamines also can be used as the (co-)chain extender. Polyamines can be used to form highly branched polyurethanes. Suitable aliphatic diamine chain extenders include diamines which can have 2 to 10 carbon atoms (i.e., $C_{2-10}$ diamines). Exemplary diamines include ethylene diamine, propanediamine, butanediamine, pentanediamine, hexanediamine, heptanediamine, octanediamine, m-xylene diamine, 1,4-diaminocyclohexane, 2-methylpentane diamine, and mixtures thereof. Alkanolamine chain extenders including ethanolamine and the like also can be used.

To obtain silicone characteristics, a polysiloxane such as a polydialkylsiloxane can be reacted with the diisocyanate, the chain extender, and the polycarbonate polyol as described above to provide the present copolymers. The polysiloxane can be a linear polydialkylsiloxane such as polydimethylsiloxane (PDMS). The molecular weight of the polysiloxane can be from about 500 Da to about 30000 Da, preferably from about 500 Da to about 8000 Da, and more preferably from about 1000 Da to about 2500 Da. The polysiloxane can have viscosities between about 10 centistokes and about 2000 centistokes. The polysiloxane can have different reactive end groups such as hydroxy groups, amino groups, isocyanate groups, and combinations thereof. In some embodiments, the polysiloxane is a diol, preferably one having $C_{1-6}$ hydroxyalkyl terminal groups. In certain embodiments, the polysiloxane can be a polydimethylsiloxane (PDMS) having hydroxypropyl terminal groups. In a particular embodiment, the polysiloxane can be an α,ω-(hydroxy propyl) polydimethylsiloxane having the formula:

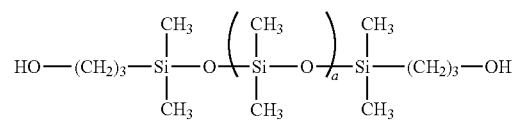

wherein a can be an integer from 3 to 100. In some embodiments, the polysiloxane also can be a copolymer, for example, a hydroxy-terminated polydimethysiloxane polyoxyethylene copolymer. However, better hydrolytic durability can be expected when the polysiloxane does not include Si—O—C linkages.

The present copolymers typically comprise at least about 5% by weight of polysiloxane. In certain embodiments, the copolymers can include greater than about 10% by weight, greater than about 15% by weight, greater than about 18% by weight, greater than about 20% by weight, greater than about 25% by weight, greater than about 30% by weight, greater than about 40% by weight, greater than about 50% by weight, or greater than about 60% by weight of polysiloxane. The present copolymers usually comprise a higher molar ratio of either or both of the polysiloxane and the polycarbonate polyol compared to the polyisocyanate, such that the polysiloxane and/or the polycarbonate can function as terminating groups in addition to being incorporated in the copolymer as internal segments. For example, the present copolymers can comprise a high molar ratio of the dihydroxy-terminated polysiloxane such that the copolymers have siloxane terminating segments. The hardness of the copolymers can be varied by increasing the amount of the diol chain extender. The chain extender(s) usually comprise less than about 10% by weight, for example, about 5% by weight, of the copolymer.

In some embodiments, a chain terminator can be added to react with the diisocyanate, the polycarbonate diol, the polysiloxane, and the diol chain extender. A chain terminator usually only has one reactive group; as such, its incorporation into the copolymer will terminate further chain extension. In certain embodiments, the chain terminator can be a monofunctional siloxane or polysiloxane, and the reactive end group can be selected from a hydroxy group, an amino group, and an isocyanate group. In particular embodiments, the chain terminator can be a monohydroxy-functionalized low molecular weight siloxane, for example, a heptamethyltrisiloxane modified with one hydroxy group. Accordingly, incorporation of the monofunctional siloxane chain extender also provides the copolymers with siloxane terminating segments.

In some embodiments, the reaction can be performed neat, that is, in the absence of solvents. In such embodiments, the polyisocyanate, the polycarbonate polyol, and/or the polysiloxane can be selected with due consideration to the viscosity of the molten mixture in the polymerization step. Specifically, a high-viscosity molten mixture can hinder the effective dispersion of the various components, which can lead to a low-yield reaction.

In alternative embodiments, the reaction can be performed in one or more solvents. In these embodiments, the polyisocyanate, the polycarbonate polyol, and/or the polysiloxane used can have higher viscosities, given that one or more solvents can be used to reduce the viscosity of the reaction mixture. Suitable solvents that can be used include acetone, methylethylketone, dimethylformamide, dimethyacetamide, ethylene carbonate, propylene carbonate, diglyme, N-methylpyrrolidone, ethyl acetate, ethylene and propylene glycol diacetates, alkyl ethers of ethylene and propylene glycol monoacetates, toluene, xylene and sterically hindered alcohols such as t-butanol and diacetone alcohol. Polar solvents such as dimethyacetamide can be preferred.

In addition to the reactive components (i.e., the diisocyanate, the chain extender(s), the polycarbonate polyol, the polysiloxane, and the optional chain terminators) described above, non-reactive additives also can be incorporated into the copolymer to provide additional properties. Such additives can include, but are not limited to, viscosity modifiers, surfactants, curing agents, antioxidants, plasticizers, stabilizers, colorants, flame retardants, and so forth, as known by those skilled in the art.

In particular, the present copolymers can include an antimicrobial agent which is incorporated into the copolymer prior to the complete polymerization of the copolymer. The resulting copolymers when fabricated into implantable medical devices can be more resistant to bacterial growth on the device surface and development of biofilms, thereby minimizing risks of foreign body-induced infections. More specifically, the antimicrobial agent can be a silver additive associated with a carrier. For example, the additive can include silver ions associated with a phosphate or a water-soluble silica glass powder carrier. The carrier can protect the silver ion from discoloration when exposed to heat, humidity and/or light. Carriers of particular interest include zeolites, phosphates and soluble silicates, among others.

Accordingly, in some embodiments, the silver ion carrier can be zirconium phosphate, and the antimicrobial additive can be ALPHASAN® RC 2000 (Miliken and Co., Spartanburg, S.C.), which is a zirconium phosphate-based ceramic ion-exchange resin containing silver. In some embodiments, the silver ion carrier can be a water-soluble silicate such as sodium silicate or potassium silicate. For example, the antimicrobial additive can be IONPURE® IPL (Ishizuka Glass Co., Naguya, Japan), which consists of a water-soluble type glass, in the form of a fine powder, and containing by weight about 1.4-2.2% elemental silver. Accordingly, in some embodiments, the present copolymers can include at least about 0.1%, about 0.5%, about 1.0% or about 2.0% silver ion by weight. Alternatively, the present copolymers can include at least about 1.0%, about 2.0%, about 4.0%, about 6.0%, about 8.0%, or about 10.0% by weight of the antimicrobial additive (that is, the combined weight of the silver ion and the carrier).

Embodiments of the present copolymers incorporating an antimicrobial additive can have a low to zero level of leaching of the incorporated silver ions. This non-leaching property reduces the risk of collateral cell death when the present copolymers are used to fabricate implantable medical devices. To prevent the silver ions from being leached out of the copolymer, the silver ions can be associated with a carrier as described above. Without wishing to be bound to any particular theory, it is believed that the addition of barium sulfate and/or micronized silica (such as SYLYSIA® 340, Silysiamont SpA, Milan, Italy) also can help reduce leaching of the silver ions. The absence of leaching of the silver ions from the copolymer can be confirmed by performing a Disk Diffusion (Kirby-Bauer) Susceptibility Test, in which a disk composed of the present copolymer with a silver-containing agent incorporated therein is placed in a microbial culture, and observing the lack of a zone of inhibition forming around the disk.

In most embodiments, the present copolymers generally are obtained from a one-step reaction of reactants comprising a diisocyanate, a polycarbonate diol, a polysiloxane, a $C_{2-8}$ diol chain extender, and optionally a chain terminator, where the diisocyanate, the polycarbonate diol, the polysiloxane, the $C_{2-8}$ diol chain extender, and the optional chain terminator are as described herein. In some embodiments, one or more additives can be added into the reaction mixture. For example, all the components (including both reactive and non-reactive additives) can be added sequentially or simultaneously into a reaction vessel and admixed thoroughly to ensure the homogeneity of the reaction mixture before the polymerization catalyst is added. The catalyst typically is either stannous octoate or dibutyltin dilaurate. After the catalyst has been added, the temperature of the reaction mixture is monitored, and the mixing of the components ceases when a predefined temperature is reached. In most embodiments, the mixing can be stopped before the reaction mixture reaches about 90° C., preferably before the reaction mixture reaches about 85° C., and most preferably, when the reaction mixture reaches about 75° C. The reaction can take place under an inert atmosphere (e.g., nitrogen), and can be conducted neat or in solution-phase. The one-step synthesis streamlines and lowers the costs of manufacturing, and the resulting copolymers exhibit desirable properties as demonstrated in the Examples hereinbelow.

In alternative embodiments, a multi-step synthesis can be used where the diisocyanate is reacted with the polycarbonate diol and the polysiloxane to provide a prepolymer. The amount of any unreacted diisocyanates is then determined, and an appropriate amount of chain extenders, polycarbonate diols, polysiloxanes, and/or chain extenders is added to react with the prepolymer to provide the present copolymers with the desired terminating segments.

After the reaction mixture reaches the predefined temperature, the admixing stops and the copolymer is poured out of the reaction vessel. To ensure that all diisocyanates in the reaction mixture are reacted, the reaction mixture can be cured, for example, by heating in an oven for a suitable period of time. In certain embodiments, the reaction mixture can be cured at an elevated temperature (greater than about 100° C., e.g., about 110° C.) for about 4 hours. The resulting copolymer can have molecular weights between about 200 kDa and about 350 kDa, and can have desirable properties including one or more of high pressure resistance, high tensile-strength, good chemical resistance, high elongation and elasticity, and a low coefficient of friction.

After curing, the reaction mixture comprising the present copolymer can be cooled for a certain period of time. For example, after curing, the reaction mixture can be cooled for at least two days. The reaction mixture then can be processed, for example, by extrusion, into powder or pellet form. In preferred embodiments, the reaction mixture is first chopped into granules, then pelletized by extrusion. For many applications, it can be desirable to have a silicone-urethane copolymer that can be melt-processed (e.g., by extrusion, injection molding, or compression molding) into pellet form, where the polymer pellets are larger than a certain size threshold. For example, it can be desirable that the silicone-urethane copolymer can withstand conventional extrusion pelletization conditions (which include high temperature and high pressure) such that instead of forming a fine powder, the copolymer can be pelletized into pellets having a diameter of at least 3 mm, at least 5 mm, or at least 8 mm.

The following examples are provided to illustrate further and to facilitate the understanding of the present teachings and are not in any way intended to limit the invention.

EXAMPLES

Copolymers according to the present teachings were made and tested as described below. Specifically, HMDI was reacted with a polycarbonate diol (Desmophen® C2200 from Bayer MaterialScience), a linear polysiloxane (PDMS) with hydroxy terminal end groups (Silmer® OH DI-50 from Siltech Corporation, Canada), and 1,4-butanediol in the presence of a tin catalyst (e.g., stannous octoate). Batches having between about 2 wt. % and about 20 wt. % of the polysiloxane were made and tested.

Films were cast from the 2%, 5%, 10%, and 20% batches by dissolving the pellets in dimethyl acetamide (DMAC). The films were then conditioned and evaluated on an Instron instrument. The results are listed below.

| | | Silicone/Urethane Polymers | | | | | |
|---|---|---|---|---|---|---|---|
| Lot # | % PDMS | Ultimate Tensile Strength/psi | % Elongation | Stress @ 50%/psi | Stress @ 100%/psi | Stress @ 200%/psi | Stress @ 300%/psi |
| A | 2 | 5877 | 610 | 377 | 539 | 894 | 1558 |
| B | 5 | 5104 | 755 | 376 | 540 | 843 | 1298 |
| C | 10 | 6099 | 793 | 353 | 502 | 802 | 1273 |
| D | 20 | 4128 | 537 | 316 | 448 | 770 | 1384 |

Additional 5% batches were made and tested. The results are summarized below.

| | Silicone Polyurethane Results | | |
|---|---|---|---|
| | Melt Index g/10 min | | Shore |
| Lot# | Granules @ 215° C. | Pellets @ 205° C. | Hardness A scale |
| E | 3.03 | 3.53 | 79 |
| F | 6.23 | 1.52 | 77 |
| G | 6.13 | 3.18 | 78 |

The present teachings can be embodied in other specific forms without departing from the spirit or essential characteristics thereof. The foregoing embodiments are therefore to be considered in all respects illustrative rather than limiting on the present teachings described herein. The scope of the present teachings is thus indicated by the appended claims rather than by the foregoing description, and all changes that come within the meaning and range of equivalency of the claims are intended to be embraced therein.

What is claimed is:

1. A silicone-urethane copolymer obtained from a one-step reaction of reactants comprising a diisocyanate, a polycarbonate diol, a polysiloxane, and a $C_{2-8}$ diol chain extender, wherein the copolymer comprises polycarbonate internal segments, polysiloxane internal segments, polyurethane internal segments, and siloxane terminating segments, and wherein the copolymer comprises between about 5% by weight and about 30% by weight of polysiloxane.

2. The copolymer of claim 1, wherein the polysiloxane is a dihydroxy-terminated polysiloxane.

3. The copolymer of claim 1, wherein the polysiloxane is dihydroxyalkyl-terminated polydialkylsiloxane.

4. The copolymer of claim 1, wherein the diisocyanate is selected from an aliphatic diisocyanate, an alicyclic diisocyanate, and an alicyclic-aliphatic diisocyanate.

5. The copolymer of claim 1, wherein the reactants further comprise a monofunctional siloxane chain terminator.

6. The copolymer of claim 1 comprising an antimicrobial agent.

7. The copolymer of claim 6, wherein the antimicrobial agent comprises silver ions associated with a zirconium phosphate carrier or a silver-containing silica glass powder.

8. The copolymer of claim 7, wherein the copolymer further comprises at least one of barium sulfate and micronized silica.

9. A method of making the silicone-urethane copolymer of claim 1, the method comprising:
   admixing a reaction mixture comprising a diisocyanate, a polycarbonate diol, a polysiloxane, and a $C_{2-8}$ diol chain extender under an inert gas in the presence of a catalyst to initiate a one-step polymerization reaction; and
   terminating the admixing step when the reaction mixture reaches a predefined temperature.

10. The method of claim 9, wherein before adding the catalyst, the method comprises adding at least one additive to the reaction mixture.

11. The method of claim 10, wherein the additive is an antimicrobial agent.

12. The method of claim 11, wherein the antimicrobial agent comprises silver ions associated with a zirconium phosphate carrier or a silver-containing silica glass powder.

13. The method of claim 12, wherein the method further comprises adding at least one of barium sulfate and micronized silica before adding the catalyst.

14. The method of claim 9, wherein the polymerization reaction is conducted in a polar solvent.

15. The method of claim 9, wherein the polymerization reaction is conducted in the absence of a solvent.

16. The method of claim 9, wherein the predefined temperature is less than 95° C.

17. The method of claim 9, wherein the predefined temperature is less than 85° C.

18. The method of claim 9, comprising curing the reaction mixture at a temperature greater than about 110° C. after terminating the admixing step.

19. The copolymer of claim 1, wherein the copolymer comprises a polycarbonate internal segment directly linked via a urethane bond to a polyurethane internal segment.

20. The copolymer of claim 1, wherein the copolymer comprises a polyurethane internal segment having a first end and a second end, wherein the first end comprises a urethane bond directly to a polycarbonate internal segment and the second end comprises a urethane bond directly to a polysiloxane internal segment.

* * * * *